United States Patent [19]

Matsumoto et al.

[11] Patent Number: 5,275,588
[45] Date of Patent: Jan. 4, 1994

[54] ARTICLE HAVING TARGET PART FOR ADHERING AND METHOD FOR PRODUCING IT

[75] Inventors: Mutsuo Matsumoto, Yamatotakada; Yasuyoshi Murotani, Fujiidera; Hidenori Takemiya, Nara, all of Japan

[73] Assignee: Nitta Gelatin Inc., Osaka, Japan

[21] Appl. No.: 762,110

[22] Filed: Sep. 19, 1991

[51] Int. Cl.$^5$ .................. A61F 13/20; A61F 13/15
[52] U.S. Cl. ..................... 604/372; 604/358; 604/389; 604/390
[58] Field of Search ............ 128/155; 604/358, 385.1, 604/386, 389, 390, 372; 602/57; 524/274, 488, 270, 272, 277, 487; 428/352, 355

[56] References Cited

U.S. PATENT DOCUMENTS

| | | | |
|---|---|---|---|
| 4,296,750 | 10/1981 | Woon et al. | 604/389 |
| 4,419,494 | 12/1983 | Puletti et al. | 524/274 |
| 4,662,875 | 5/1987 | Hirotsu et al. | 604/389 |
| 4,813,947 | 3/1989 | Korpman | 604/390 |
| 5,149,741 | 9/1992 | Alper et al. | 524/274 |

FOREIGN PATENT DOCUMENTS

| | | |
|---|---|---|
| 0440163A3 | 8/1991 | European Pat. Off. . |
| 2-135175 | 5/1990 | Japan . |
| 2054350A | 2/1981 | United Kingdom . |
| 2135568A | 9/1984 | United Kingdom . |

OTHER PUBLICATIONS

Irving Sax and Richard Lewis, Sr., "Hawleys Condensed Chemical Dictionary, 11th Ed.", pp. 1233–1234.

*Primary Examiner*—David Isabella
*Assistant Examiner*—A. Zuttarelli
*Attorney, Agent, or Firm*—Lowe, Price, Leblanc & Becker

[57] ABSTRACT

An article having a target part for adhering, wherein the part adheres with an adhering face of a tab in a repeatedly releasable manner in which the target part is made of a hot melt resin composition. Thus, the total cost for making the target part is reduced.

2 Claims, 7 Drawing Sheets

ARTICLE HAVING TARGET PART FOR ADHERING AND METHOD FOR PRODUCING IT

BACKGROUND OF THE INVENTION

1. Field of the Invention

The present invention relates to an article having a target part for securing portions together and to a method for manufacturing the target part.

2. Description of the Background Art

A representative example of the article having a target part for securing portions together is a disposable diaper. A securing system of this type consists of a tab having an adhering face and a target part to which the tab adheres to allow the diaper to be put on easily and removed. The target part is usually located at an outer face of the front side of a diaper. Several tabs are arranged at both sides of the inner face of the diaper are able to adhere to and be removed from the target part. The diaper is put on the lower torso of a person's body, adjusted for comfort, then fixed and used. When the diaper is removed, the fastening system is released. Because the surface of the base material of the target part is prepared to satisfy such properties as water-nonpermeability, flexibility, and fashion/appearance, the surface is not suitable for repeatedly attaching and removing the tab to the target part.

The target part, for example as shown in FIG. 4, is made by attaching a resin sheet 202 on a base 200 by means of an adhering agent 201. FIG. 5 shows one example of a process for forming the target part. A continuously supplied oriented polypropylene film 27 is continuously coated with a hot melt adhesive 28 stored at 28, from a coating gun 29, to the whole of a rear face of the film 27. This film is cut to a proper size and attached to a surface of polyethylene film 20, becoming the outer layer of the polyethylene film 20. Thus, the target part is formed on the outer layer of the polyethylene film 20. Another method for forming the target part is to purchase an adhering tape with a surface that has been subjected to mold-releasing treatment (on the back of which a release paper is stuck), and attaching the tape to the outer face of the polyethylene film.

In the forementioned conventional procedure, the material cost for making the target part may be high. The process for making it may also be complex and, therefore, hence the total cost is usually high.

SUMMARY OF THE INVENTION

Accordingly, the first object of the present invention is to provide an article with a target part for securing portions of the article and that reduces the total cost.

Another object is to provide a method for continuously producing such an article.

To solve the first object, an article of the present invention having a target part for repeatably attaching and removing to the adhering face of the tab is characterized by forming the target part from a hot melt resin composition.

To solve the second object, a method is provided for continuously producing such an article, which during processing has a continuously moving base surface, characterized by directly coating this hot melt resin composition on the continuously moving base surface.

A system is thus provided for securing portions of an article, comprising:

a target part formed on a portion of said article; and a tab formed on another portion of said article;

wherein said tab attaches to said target area to form an impermanent adhesion which is capable of being reestablished if undone; and said target part is a discernable pattern formed from a hot melt resin composition.

DESCRIPTION OF THE PREFERRED EMBODIMENTS

Figure 1:
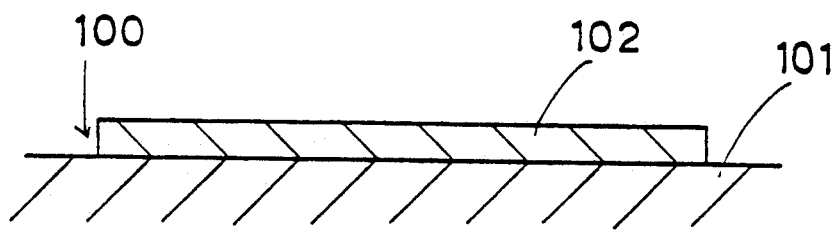
FIG. 1 is a cross-sectional view showing a target part in an article incorporating the present invention.

It is preferred that the hot melt resin composition used in the present invention should satisfy all the following conditions of 1 to 4.

1. The open time is short. Although, the shorter the open time the better, it is preferable to have an open time of 0.5 seconds or less. If the open time is longer than this range, the problem of adhesive-attaching to a press roll will occur. 2. The surface energy of the solidified matter is low. The preferred range of surface energy is from about 15 to 25 dyne/cm$^2$, for the facility in adhering the target part with the adhering face of a tab to be compatible with the facility in peeling it off. If the surface energy is greater than this range, the mold-releasing character is diminished and the tab release becomes difficult. If less than this range the tab will not adhere.

3. The adhering characteristic with a base material must be excellent. It is required that the peeling-off takes place at an interface between the tab and the target part, not at the interface between the target part and the base material.

4. A preferred blocking character would be one that ensures that the target part is not peeled off, due to attaching to other matter in a period of time between the target formation and practical use. It is also preferred that this blocking character is exhibited at about 65° C. or less.

The hot melt resin composition is prepared so as to be satisfactory for all the above-mentioned conditions by combining, in a suitable proportion, a base polymer, a tackifier resin, wax, oil, pigment, and an antioxidant.

The base resin that is used can be one or a combination of two or more of the following thermoplastic resins: a copolymer of ethylene-vinyl acetate (EVA), polystyrene-polybutadiene-polystyrene block copolymer (SBS), polystyrene-polyisoprene-polystyrene block copolymer (SIS), polystyrene-polyethylene/polybutylene-polystyrene block copolymer (SEBS), or a polyolefin-based polymer.

The tackifier resin that is used can be one or a combination of two or more of the following: an aliphatic or alicyclic hydrocarbon resins, rosin and its derivative, or a terpene-based resin.

The wax that is preferably used is a microcrystalline Fischer-Tropsch wax manufactured solely by Sasol Chemical Industries, Inc., of the Union of South Africa.

The oil that is used can be one or a combination of the following oils: paraffin-based oil or naphthene-based oil.

Additionally, if the hot melt resin composition is used in a visible place, an appropriate pigment may be added to achieve a desired color.

Among the above components, the base polymer, tackifier resin, wax, and oil are used, for example, in the following proportion. Against 100 parts by weight of a total of these four components, the base polymer is from about 20 to 40 parts by weight, the tackifier resin from about 20 to 40 parts by weight, the wax from about 30 to 50 parts by weight, and the oil from about 0 to 20 parts by weight. If an antioxidant is to be used, it is preferred to use it in a proportion of 1.0 part or less by weight against the aforementioned 100 parts. If a pigment for coloring is to be used, it is preferred to use it in a proportion of 1.0 part by weight against the aforementioned 100 parts.

Furthermore, according to the present invention, since the target part is made by a hot melt resin composition, various properties can be achieved by properly designing the hot melt resin composition. For example, the properties of adjustment of flexibility, reinforcement of a base material, and control of a peel strength, can be determined, for example, by controlling the amount of a rubber-based polymer used, by the use of a resin that has a high softening point, or by using a different combination of waxes.

A hot melt resin composition prepared with the above-described components is directly coated on a base material surface. This coating is carried out by using a common hot melt coating gun. The coating thickness may be similar to that of a common hot melt adhesive, for example, in an order of from about 50 to 200 μm. Also, since the target part is made by coating the hot melt resin composition directly onto the base, the target part can be easily formed on a continuously moving base material. Furthermore, since there is no need to lower line speed to cut the adhesive tape and the like, it is possible to increase line speed.

A mark is used to indicate the placement of the tab on the target area for a comfortable fit of the diaper. The next time a diaper is to be used, the tab can be placed directly on the target area, as indicated by the mark. Having previously determined the placement of the tab, the mark prevents having to adjust the diaper to achieve a comfortable fit each time it is used.

Where a hot melt resin composition completely coats the portion of the base material which is to become the target part, a mark indicating tab placement can be printed beforehand. The printed mark will be seen through the hot melt resin composition.

Alternatively, the mark can be drawn by a hot melt resin composition when this composition is formed. This is called screen coating. In screen coating, a screen having many small holes is used to depict the desired pattern. A hot melt resin composition is pushed through the holes onto the base, with the resulting coating formed from many small dots. Thus, the coated pattern also serves as a mark to show the position for the placement of the tab. It is possible to make various designs from the assembly of dots. By changing the pattern shape and/or the dot size, the peel strength required to remove an attached tab can be adjusted without any change in the components and combination of the hot melt resin composition.

The base material for the target part is a combination of a polyethylene film and an OPP (oriented polypropylene) film for a disposable diaper.

Article having a target part for adhering, as produced by the present invention, include a disposable diaper and a drape for medical use, but the possibilities are not limited to those described here.

The "tab" is defined in an article having a target part, as a part being arranged in another portion of the same article and having an adhering face to attach to the target part. For example, when a portion of an adhesive tape is attached to an article and the remaining portion is unattached, this unattached portion is called a tab. Furthermore, when the adhesive character of the tab is not to be used, release paper covers the tab to maintain the adhesive character of the tab. The release paper then can be peeled off to adhere the tab with the target part.

By making the target part from a hot melt resin composition, it is unnecessary to use a resin sheet which converts into the target part, resulting in decrease in the material cost and a simplification of the process. In addition, conventional continuous production line can be used.

Hereinafter, the present invention is explained in detail, referring to figures which show examples of the invention, but the present invention is not limited by the examples and figures.

Figure 4:
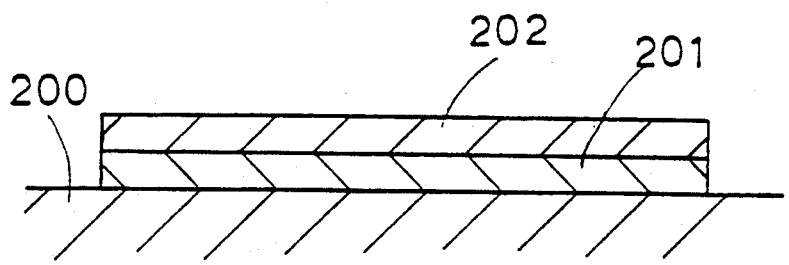
FIG. 4 is a cross-sectional view illustrating how a known target part is formed.

FIG. 1 is a cross-sectional view showing an example of an article having a target part for adhering, relating to the present invention. As seen in FIG. 1, this article 100 has a target part 102 made from a hot melt resin composition on a surface of the base material 101 and, when compared with a conventional target part shown in FIG. 4, the present invention is simplified because it lacks the resin sheet 202. Such an article 100 may be produced by either a continuous production method or a noncontinuous production method.

Figure 2:
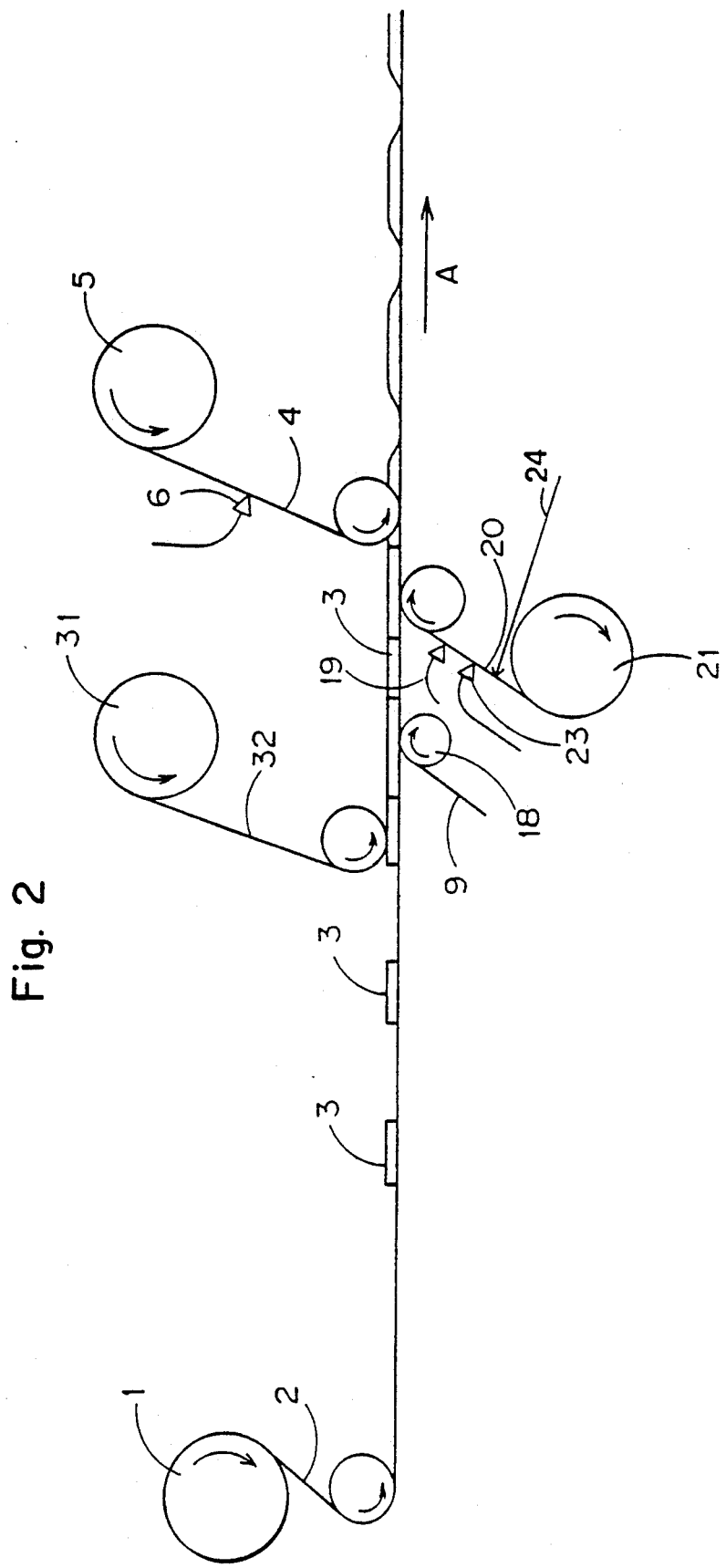
FIG. 2 is a schematic illustration of how one preferred method may be used to produce an article, according to the present invention, which has a target part for adhering.
Figure 3:
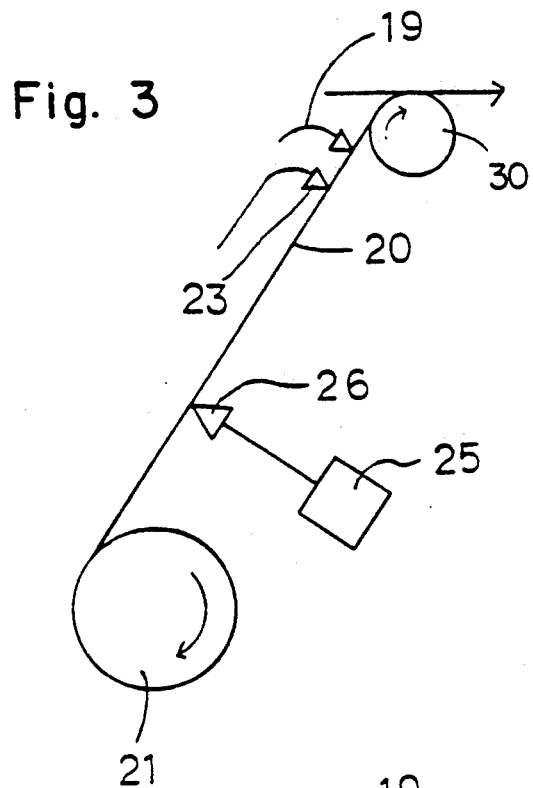
FIG. 3 is a schematic illustration showing a portion of the apparatus shown in FIG. 2.
Figure 5:
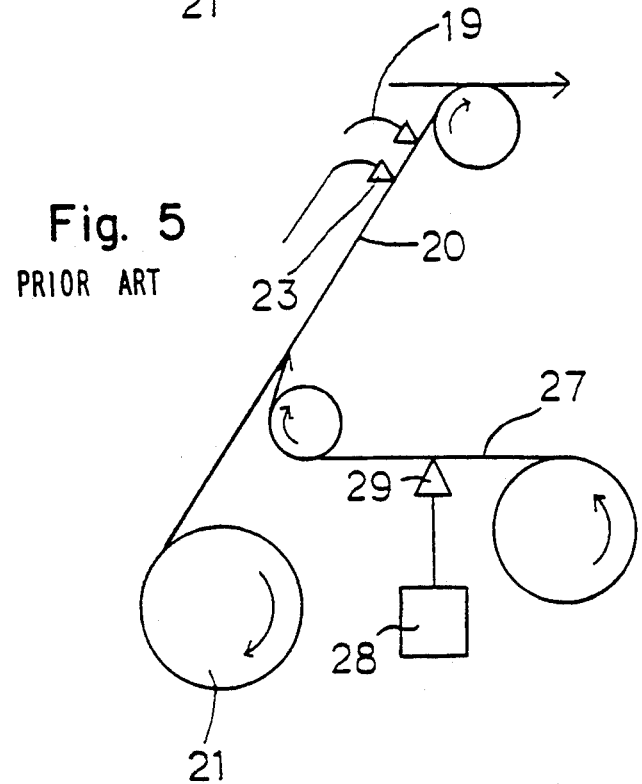
FIG. 5 is a schematic illustration showing a process for making a previous target part.

FIG. 2 shows the present invention being incorporated into a method for producing a disposable diaper. As seen in this figure, a tissue paper 2 is continuously supplied from a first roll 1 and a second tissue paper 32 is continuously supplied from a second roll 31, and a water-absorbent material 3 is placed between these tissue paper layers 2 and 32. A polyethylene film 20, which forms the back sheet, is continuously supplied from roll 21. As seen in FIG. 3, a hot melt resin composition from a source 25 thereof is coated, in a necessary amount, on the polyethylene film 20 by the coating gun 26 (as shown by 24 in FIG. 3), forming a patterned target part (not shown in the figure) on an outer surface of the polyethylene film 20. The hot melt resin is pressed to the polyethylene film by passage over a pressure roll 30 (best seen in FIG. 3). This hot melt resin composition 25 is as described above.

On the rear side of the polyethylene film 20, having the formed target, a hot melt adhesive is continuously applied from the coating guns 19 and 23. The film 20 is attached to the tissue paper 2 by the adhesive so that it greatly overhangs the tissue paper 2. An elastic band 9 is attached by the adhesive to form a stretching and shrinking part on both sides of the water-absorbent material 3. A non-woven fabric 4, continuously supplied from the roll 5, is attached to tissue paper 32 by the adhesive continuously supplied from coating gun 6 so that it greatly overhangs tissue paper 32.

Thus, a layered article is produced that comprises a combination of tissue paper 2, water-absorbent material 3, and tissue paper 32 that is placed between the polyethylene film 20 and the non-woven fabric 4. This article is cut to form a disposable diaper. Although formation of a tab having an adhering face has not been mentioned, it is carried out in the usual way.

Figure 6:
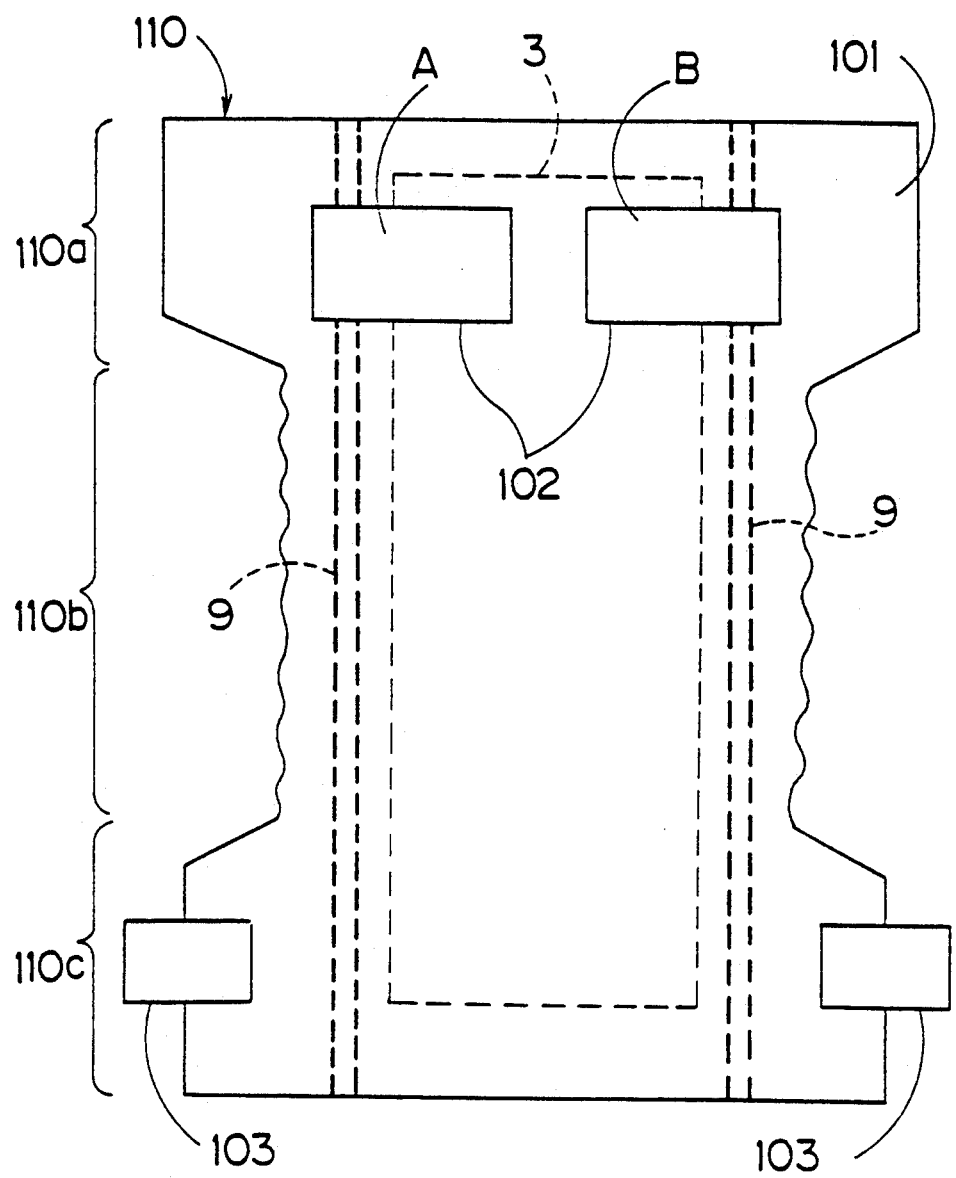
FIG. 6 is a plan view showing a disposable diaper incorporating the present invention.
Figure 7A:
FIGS. 7–13, respectively, show pattern examples of the target part for adhering.
Figure 7B:
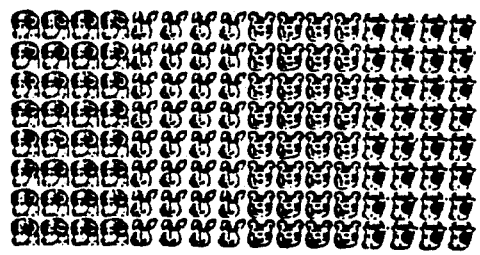
Figure 8A:
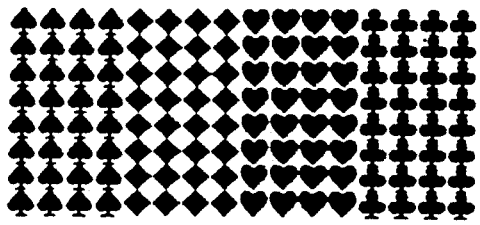
Figure 8B:
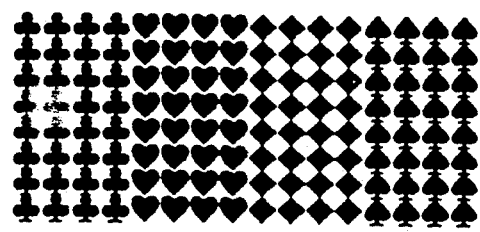
Figure 9A:
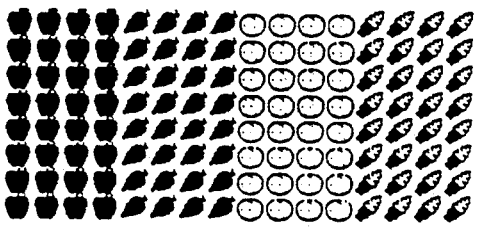
Figure 9B:
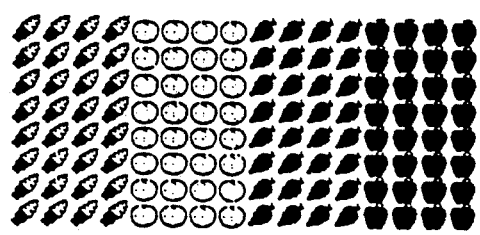
Figure 10A:
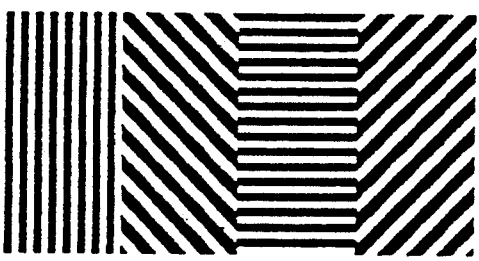
Figure 10B:
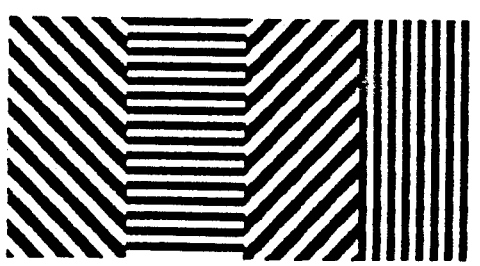

FIG. 6 shows a plan view of an example in a case where the article in the present invention is a disposable diaper. The diaper 110 is shaped similar to the letter "I", and comprises lower abdomen part 110a with two wings stretched to the left and right, the crotch part 110b constricted at the central part, and the hip portion 110c having two wings stretched to the left and right. In an area that extends from the lower abdomen 110a to the hip portion 110c, absorbent material 3 is placed between two tissue papers, so that urine, etc. is absorbed and held. On the left and right sides of the absorbent material 3, an elastic band 9 is arranged so that a contracting force operates to keep the diaper 110 in firm contact around the groin of the wearer. The tabs 103 are set at the pointed ends of two wings of the hip portion 110c. On a surface of a base material (for example, a polyethylene film) of the lower abdomen part 110a, the target parts 102 for adhering are formed of a hot melt resin composition as described above.

A mark that is on a surface of the base material 101 on a lower side of the target part for adhering 102, printed to indicate a tab-sticking position, will be seen through the hot melt resin composition. On the other hand, the mark may be drawn with the hot melt resin composition when the target part 102 is formed.

FIGS. 7-13 show sample patterns for marks on the left and right target parts 102. When the disposable diaper 110 is made, each of A and B in FIGS. 7-13 are respectively placed on the right lower abdomen and left lower abdomen. As the tab shown in FIGS. 7-13 is attached toward the center, the diaper becomes tighter, and as it is attached toward the outside, the diaper becomes looser. If the same disposable diaper is to be repeatedly used by the same wearer, once a comfortable fit for the diaper is determined the next diaper can be attached at the same mark for the same fit.

Figure 14:
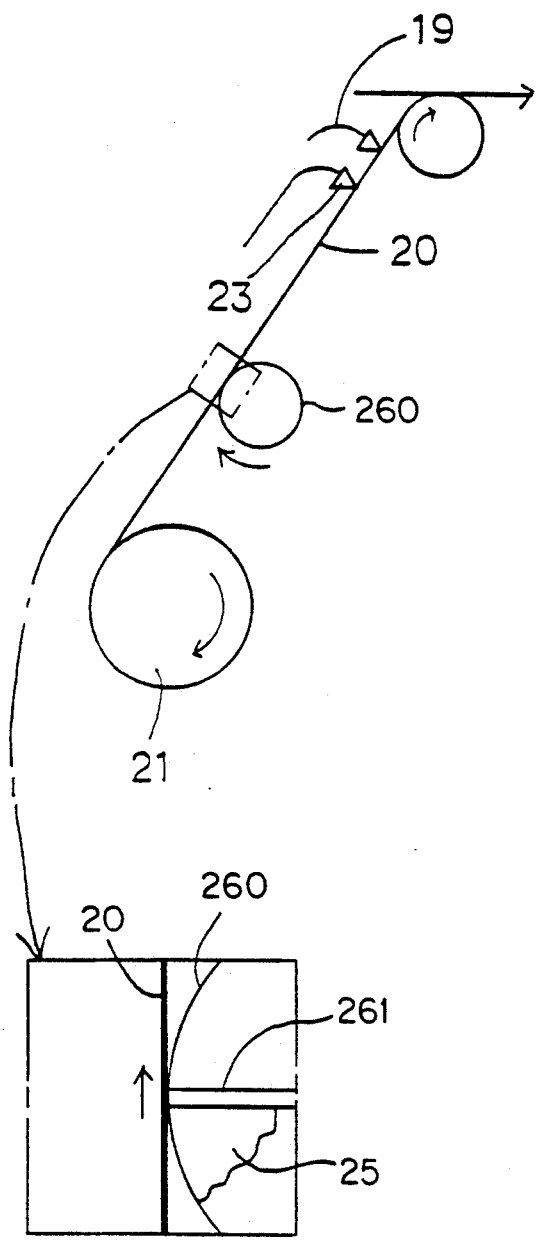
FIG. 14 is a schematic illustration of another embodiment of the apparatus shown in FIG. 3.

FIG. 14 depicts the process for a target part for adhering that is made by a screen printing of the hot melt resin composition. In place of the coating gun 26 shown in FIG. 3, there is used a cylinder type screen 260 that is arranged so as to rotate around the center axis. When the hot melt resin composition 25 is placed in the cylinder type screen 260 and is rotated, the hot melt resin composition 25 is pressed to the inner circumferencial face by a doctor blade 261, and passes through transmission holes to the outside. Thus, the hot melt resin composition 25 is coated on a surface of the base material polyethylene film 20, to form the target part. The coating pattern of the hot melt resin composition 25 is, as shown in FIGS. 7-13, for example.

The cylinder type screen 260 is designed so that one circumference length corresponds to the length of the disposable diaper 110, and the transmission holes are arranged, for example in a pattern shown in FIGS. 7-13, in a part of a circular arc as long as the target part. Thus, screen printing can be carried out by rotating the screen 260 in correspondence with the velocity of a disposable diaper-producing line, and a process for making the target part for adhering 102 can be included in the disposable diaper-producing line. A different method for integrating screen printing into the disposable diaper production line may also be used.

Hereinafter, practical examples and comparative examples of the present invention are described but this invention is not limited to the discussed examples.

EXAMPLE 1

The hot melt resin composition used for making the target part for adhering depicted in FIG. 2 had the following composition:

base polymer: EVA (EV-220, made by Mitsui Dupont Polychemical Co., Ltd.) - - - 33 parts by weight tackifier resin: $C_9$-based hydrogenated petroleum resin (Akron M115, made by Arakawa Chemical Industries, Ltd.) - - - 22 parts by weight wax: microcrystalline wax (Sasol H 1, made by Sasol Chemical Industries, Ltd.) - - - 45 parts by weight antioxidant (age resistor): (Irganox 1010, made by Ciba-Geigy Japan, Ltd.) - - - 0.4 parts by weight These components were well mixed in a melting step at 140° C., and coated at a thickness of 150 μm on a polyethylene film of thickness 40 μm, to form a target part.

EXAMPLE 2

The procedure of example 1 was repeated except that the hot melt resin composition was changed to the combination described below.

The hot melt resin composition was:

base polymer: SIS (SL-102, made by Nippon Zeon Co., Ltd.) - - - 22 parts by weight tackifier resin: hydrogenated petroleum resin (Escorez 5300, made by Tonex Co., Ltd) - - - 25 parts by weight oil: paraffin-based oil (PW-90, made by Idemitsu Kosan Co., Ltd.) - - - 10 parts by weight wax: microcrystalline wax (Sasol H 1, made by Sasol Chemical Industries, Ltd.) - - - 43 parts by weight antioxidant (age resister): (Irganox 1010, made by Ciba-Geigy Japan, Ltd.) - - - 0.4 parts by weight ultraviolet rays absorbent (JF-77, made by Johoku Chemical Co., Ltd.) - - - 0.2 parts by weight

EXAMPLE 3

The procedure of example 1 was repeated except that the hot melt resin composition was changed to the combination described below.

The hot melt resin composition was:

base polymer: SBS (Tufprene 315, made by Asahi Chemical Industry Co., Ltd.) - - - 25 parts by weight tackifier resin: hydrogenated petroleum resin (Admarv S-100, made by Idemitsu Petrochemical Co., Ltd.) - - - 25 parts by weight oil: paraffin-based oil (PW-90, made by Idemitsu Kosan Co., Ltd.) - - - 5 parts by weight wax: microcrystalline wax (Sasol H1, made by Sasol Chemical Industries, Ltd.) - - - 45 parts by weight antioxidant (age resister): (Irganox 1010, made by Ciba-Geigy Japan, Ltd.) - - - 0.4 parts by weight ultraviolet rays absorbent (JF-77, made by Johoku Chemical Co., Ltd.) - - - 0.2 parts by weight

EXAMPLE 4

Figure 11A:
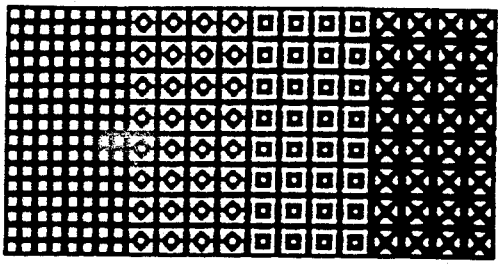
Figure 11B:
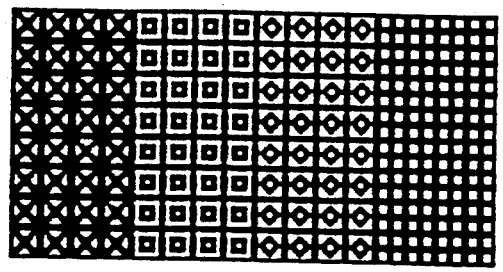
Figure 12A:
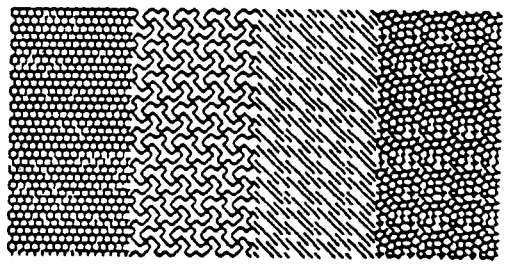
Figure 12B:
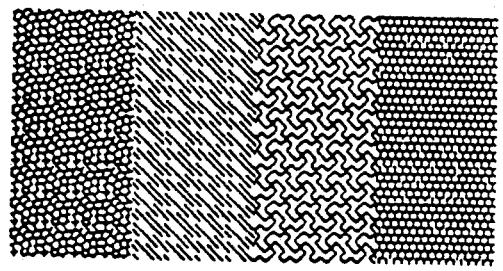
Figure 13A:
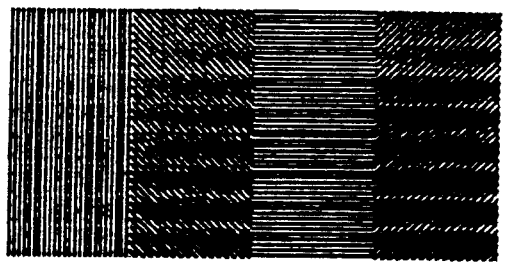
Figure 13B:
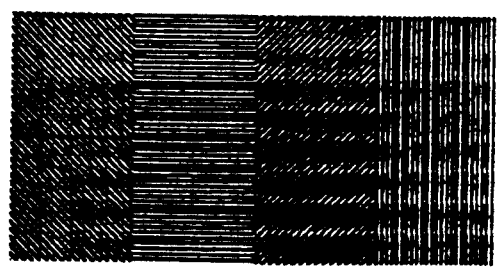

The procedure of example 1 was repeated except that the hot melt resin composition was coated in a pattern shown in FIG. 11 (refer to FIG. 14) under the conditions of a coating temperature (a screen temperature) of 110° C., a coating amount of 50 g/m², and a web speed of 100 m/minute, and using a screen printing machine (Micro Print, made by LTI GRACO Co., Ltd.).

For the disposable diapers in the above examples 1-4, the undermentioned properties of from (1) to (5) were investigated. Results are shown in Table 1.

(1) Surface energy.

It was investigated by a method of measuring a contact angle of a solid.

(2) Adhering property with tab (or fastening tape).

The peel strength between the tab (for commercial articles, their respective fastening tape and, for the examples, a commercially-available adhesive tape, made by 3M Co., Ltd.) and the target part was investigated.

(3) Refastening property.

Similary to (2), the tab and a target part were repeatedly attached and removed. The fifth time was used for measurement of the peel strength.

(4) Open time.

In a pilot line which shows the whole of FIG. 3, a hot melt resin composition was melted at 140° C. and coated on a polyethylene film having a thickness of 40 μm in a coating thickness of 150 μm, on which a paper of fine quality was stuck. The coating was carried out with a varied line speed, then the period of time from the coating to the sticking of the paper was varied in a range of 0.1 to 1.0 second, and the longest time required for adhesion was assigned as the open time.

(5) Blocking property.

A sample was prepared by coating the hot melt resin composition of each example on a polyethylene film and, on a resin composition side of the sample, a polyethylene film was piled up. The sample stood for 24 hours in an oven at 60° C. Whether or not the piled polyethylene film and the resin composition stuck together upon examination is indicated by a cross X if it is sticking and by a circle O if it is not sticking.

For comparison to the examples of the present invention, the target tape parts of the under-described commercially-available disposable diapers were taken by cutting and subjected to examination of the above-described 1-5 properties. Results are shown in Table 1.

Comparative example 1 - - - Pampers of Proctor & Gamble Far East, Inc.

Comparative example 2 - - - Ultra Mooney of Uni-Charm Corporation.

Comparative example 3 - - - Merries of Kao Corporation.

TABLE 1

|  | Example 1 | Example 2 | Example 3 | Example 4 | Comparative example 1 | Comparative example 2 | Comparative example 3 |
|---|---|---|---|---|---|---|---|
| Surface energy (unit: dyne/cm) | 19.5 | 19.1 | 22.7 | 19.7 | 20.3 | 23.5 | 20.5 |
| Adhering property with tab (unit: gf/25 mm) | 460 | 430 | 450 | 480 | 420 | 440 | 400 |
| Refastening property (unit: gf/25 mm) | 400 | 410 | 420 | 440 | 470 | 420 | 400 |
| Open time (unit: second) | 0.2 or less | 0.2 or less | 0.2 or less | 0.2 or less | — | — | — |
| Blocking property | o | o | o | o | — | — | — |

As seen in these results, the examples of the present invention exhibited of no problems and the target parts were formed with less materials and by a simpler process than those for commercially-available articles.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

What is claimed are:

1. A system for securing portions of an article, comprising:

a target part comprising a hot melt resin composition comprising a synthetic Fischer-Tropsch wax and having an open time of 0 to 0.5 seconds, applied on a first portion of said article in a discernable pattern to guide a user of the article; and a tab formed on a second portion of said article, to enable attachment of said second portion to said first portion solely by coaction with and in a selected relationship with the hot melt composition pattern, whereby said tab attaches to said target area to form an impermanent adhesion which can be terminated and reestablished repeatedly.

2. A system for securing portions of an article, according to claim 1, wherein:

said hot melt resin composition, per a total weight of 100 parts, comprises a base polymer in an amount of 20 to 40 parts by weight;

a tackifier resin in an amount of 20 to 40 parts by weight;

said synthetic Fischer-Tropsch wax in an amount of 30 to 50 parts by weight; and an oil in an amount of 0 to 20 parts by weight.

* * * * *